United States Patent [19]

McFarland

[11] Patent Number: 4,744,353
[45] Date of Patent: May 17, 1988

[54] METHOD FOR ATTACHING SOFT TISSUE TO BONE TISSUE

[76] Inventor: Joseph R. McFarland, 507 Palo Alto Dr., Vancouver, Wash. 98661

[21] Appl. No.: 853,754

[22] Filed: Apr. 18, 1986

[51] Int. Cl.[4] ............................................. A61F 5/04
[52] U.S. Cl. ........................... 128/92 VD; 128/303 R; 81/490
[58] Field of Search .......... 128/92 R, 92 VD, 92 VZ, 128/303 R, 92 V; 81/490

[56] References Cited

U.S. PATENT DOCUMENTS

| 516,294 | 3/1894 | Britton | 81/490 |
|---|---|---|---|
| 2,200,120 | 4/1938 | Nauth | 128/92 VD |
| 4,381,770 | 5/1983 | Neufeld | 128/92 XV |
| 4,421,112 | 12/1983 | Mains et al. | 128/92 XV |
| 4,450,835 | 5/1984 | Asnis et al. | 128/92 XV |
| 4,622,960 | 11/1986 | Tam | 128/92 VK |

FOREIGN PATENT DOCUMENTS

| 3411891 | 10/1985 | Fed. Rep. of Germany | 128/92 VD |
|---|---|---|---|
| 2147504 | 5/1985 | United Kingdom | 128/92 XV |

OTHER PUBLICATIONS

"Treatment of Fracture of the Neck of the Femur", by E. T. Bailey, M.D., *The Lancet*, Feb. 13, 1937.
*Fractures and Joint Injuries*, vol. II, pp. 458, 459, by R. Watson–Jones, 1944.
*Campbell's Operative Orthopedics*, Fifth Edition, vol. I, A. H. Crenshaw Editor, 1971.

Primary Examiner—Stephen C. Pellegrino
Assistant Examiner—Ralph Lewis
Attorney, Agent, or Firm—Chernoff, Vilhauer, McClung & Stenzel

[57] ABSTRACT

Apparatus and a method for attaching soft tissue to bone in a surgical operation, particularly in suturing a portion of a shoulder joint socket to the rim of the glenoid cavity of a scapula. A drilling guide includes a pair of convergent tubes and a handle supporting them, and a locater rod is used to aid in holding the drilling guide so that intersecting holes can be drilled from opposite sides of the glenoid rim. A suture is pushed into one of the intersecting holes and pulled out from the other using a double hook to anchor a suture to the glenoid rim.

3 Claims, 3 Drawing Sheets

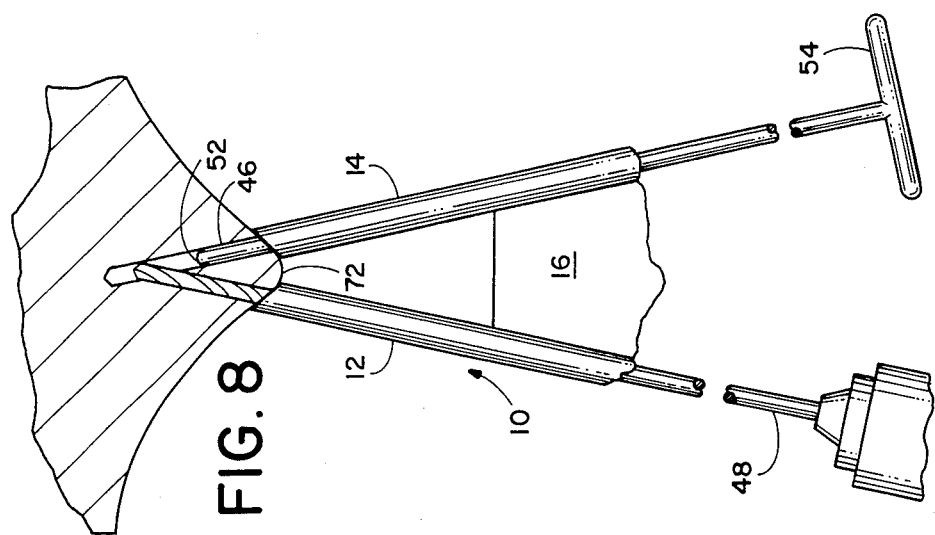
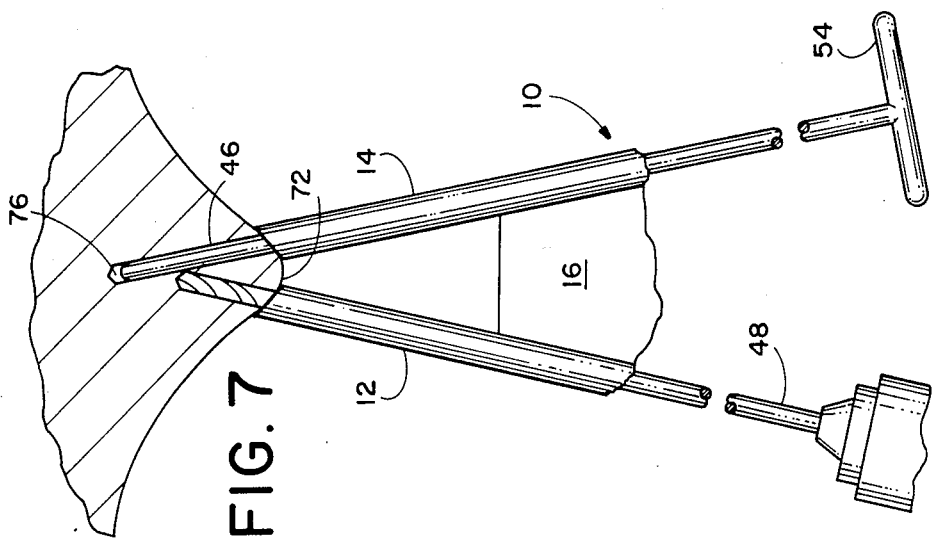
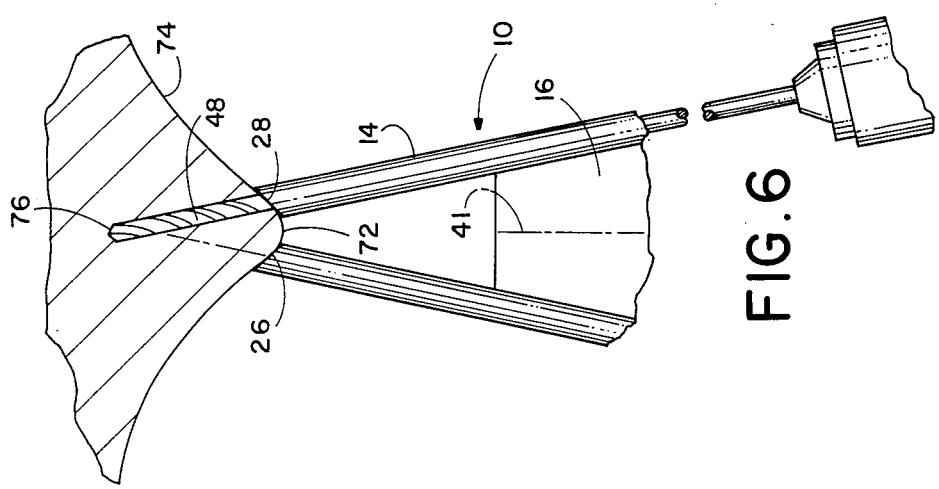

METHOD FOR ATTACHING SOFT TISSUE TO BONE TISSUE

BACKGROUND OF THE INVENTION

The present invention relates to surgical attachment of soft tissue to bone tissue, and particularly to a tool and method for its use in performing the Bankart repair procedure to reattach a torn shoulder joint capsule to the scapula.

Dislocation of a shoulder joint often results in connective tissue of the shoulder joint capsule being torn free from the rim of the glenoid cavity of the scapula. Resultant weakening of the joint often leads to recurrence of the dislocation. In a surgical procedure called the Bankart operation, muscle surrounding the shoulder joint is cut and moved aside to give direct access to the attachment of the shoulder joint capsule to the anterior rim, or labrum, of the glenoid cavity of the scapula. Three or four holes are made through the glenoid rim, and sutures are passed through the holes and used to attach a portion of the capsule to the scapula. The entire procedure is described in greater detail in such medical references as *Campbell's Operative Orthopedics*, published by the C. V. Mosby Company of St. Louis, Mo.

Using previously available tools and methods, it has been difficult to provide the necessary holes extending through the rim of the glenoid cavity. Such holes in the past have been made by use of hammered spikes, dental drills with offset heads, or pincers-like piercing instruments. Use of an offset drill is difficult because of the slippery surfaces into which the necessary holes must be drilled. There has, then, been no reliable, easy way to provide a passage for sutures through the anterior glenoid rim which leaves a dependably strong enough solid body of bone to which to attach a suture to reattach the joint capsule to the rim of the glenoid cavity. As a result, the Bankart procedure has been difficult to perform, even though it is often preferred because of the excellent results it produces.

Various ways of attaching soft tissue to bone have been described in the past for use particularly in other parts of the human body. For example, United Kingdom patent application GB No. 2147504A of Hourahane discloses an arcuate frame to which is attached a probe for insertion through soft tissue surrounding a knee joint, together with a drill guide, for providing intersecting bores in bones and inserting sutures through the bores to attach soft tissue to a bone. Another drill guide disclosed by Hourahane is useful for drilling intersecting holes in certain bones where points of the drill guide can be driven into the bone to stabilize the tool. The apparatus disclosed by Hourahane, however, is not well adapted for use in performing the Bankart operation, because of its large size and the thick layer of muscle and connective tissue which must be moved aside to gain access to the glenoid rim.

Asnis et al. U.S. Pat. No. 4,450,835 discloses a tool which may be used to guide in the drilling of intersecting bores, but there is no disclosure of how such a tool could be used for repair of a shoulder joint.

Mains et al. U.S. Pat. No. 4,421,112 discloses use of a drilling guide in connection with osteotomy of the tibia, in which converging bores are drilled, using a pin extending into an earlier drilled bore to hold a guide for a drill used to form the later bore.

Neufeld U.S. Pat. No. 4,381,770 discloses another drilling guide which is held in the required position for drilling a subsequent bore by a rod extending into an earlier drilled bore. The Neufeld disclosure relates to repair of a broken femur, however, and the drilling guide does not appear to be applicable to repair of a shoulder injury.

None of the above-mentioned previously-known devices or methods is particularly well adapted for use in performing the Bankart operation on a shoulder joint.

What is needed, therefore, is a tool useful for guiding a small drill to bore a passageway through the rim of the glenoid cavity of a scapula in order to provide a strong anchor point for attachment of the capsule of the shoulder joint to the scapula. Such a tool must be useful in the restricted amount of space available in the vicinity of the shoulder joint. Additionally, a method is needed for attaching sutures to the scapula securely.

SUMMARY OF THE INVENTION

The present invention provides a novel tool and a method for its use in performing a surgical operation to connect soft tissue to bone tissue. The tool and its use according to the invention overcomes the disadvantages and shortcomings of the previously-known devices and methods for attaching soft tissue to bone tissue, particularly with reference to the Bankart operation for reattaching the capsule of a shoulder joint to the scapula. The invention also provides a method for use of the tool to perform the Bankart operation in a manner which is faster and thus less traumatic to the patient than previously has been possible.

The tool provided by the present invention is a drilling guide having a pair of converging bores and an offset handle for supporting the drilling guide and providing clearance enough for the convenient use of a power-driven drill to bore intersecting holes at desirable locations in the scapula. Also provided is a locating rod which may be inserted through one of the bores into a first hole drilled in the scapula, to retain the drilling guide in a required location in which a second bore drilled in a location determined by the drilling guide will intersect the first hole in the scapula. A suture may be manipulated through the resulting passage using a special tool having a hooked end, in order to provide a strong anchor point for reattachment of the shoulder joint capsule to the glenoid rim of the scapula in a shorter time than was possible using tools previously available.

It is therefore a principal object of the present invention to provide a tool for use in creating a passage for a suture to attach the joint capsule to the scapula in performing the Bankart repair procedure for surgical correction of a damaged shoulder joint.

It is another important object of the present invention to provide a method for attaching a shoulder joint capsule to the scapula as a part of the Bankart procedure.

A principal feature of the present invention is a drill guide tool including a pair of convergent bores, together with which a locating rod is used to create a pair of intersecting holes in a portion of the scapula, so that a suture can be anchored securely in the scapula.

Another important feature of the tool provided by the invention is an offset handle facilitating manipulation of the drilling guide portion of the tool without obstructing the use of a power-driven drill to bore holes in a patient's scapula.

A further feature of a preferred embodiment of the tool of the invention is the shape of the forward end of the drill guide, which closely fits the shape of the rim of the glenoid cavity.

An important advantage of the present invention is that it facilitates making a stronger attachment of a joint capsule to the scapula than previously has been possible without ample quantities of good luck.

Another important advantage of the present invention is that it enables the Bankart shoulder repair procedure to be performed reliably in a shorter amount of time, thus reducing the amount of trauma experienced by a patient and reducing the cost of performing the procedure.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 6 is a view of the drilling guide shown in FIG. 1, together with a sectional view of a portion of a patient's left scapula, showing the use of the tool of the invention to prepare a first hole in preparation for reattaching the shoulder joint capsule to the scapula.

FIG. 7 is a view similar to that of FIG. 6, showing the boring of a second hole while the drilling guide is held in the proper location with the aid of the locating rod.

FIG. 8 is a view similar to that of FIG. 7, showing the manner of completing a second hole to intersect with the first hole in the scapula.

DETAILED DESCRIPTION OF THE INVENTION

Figure 1:
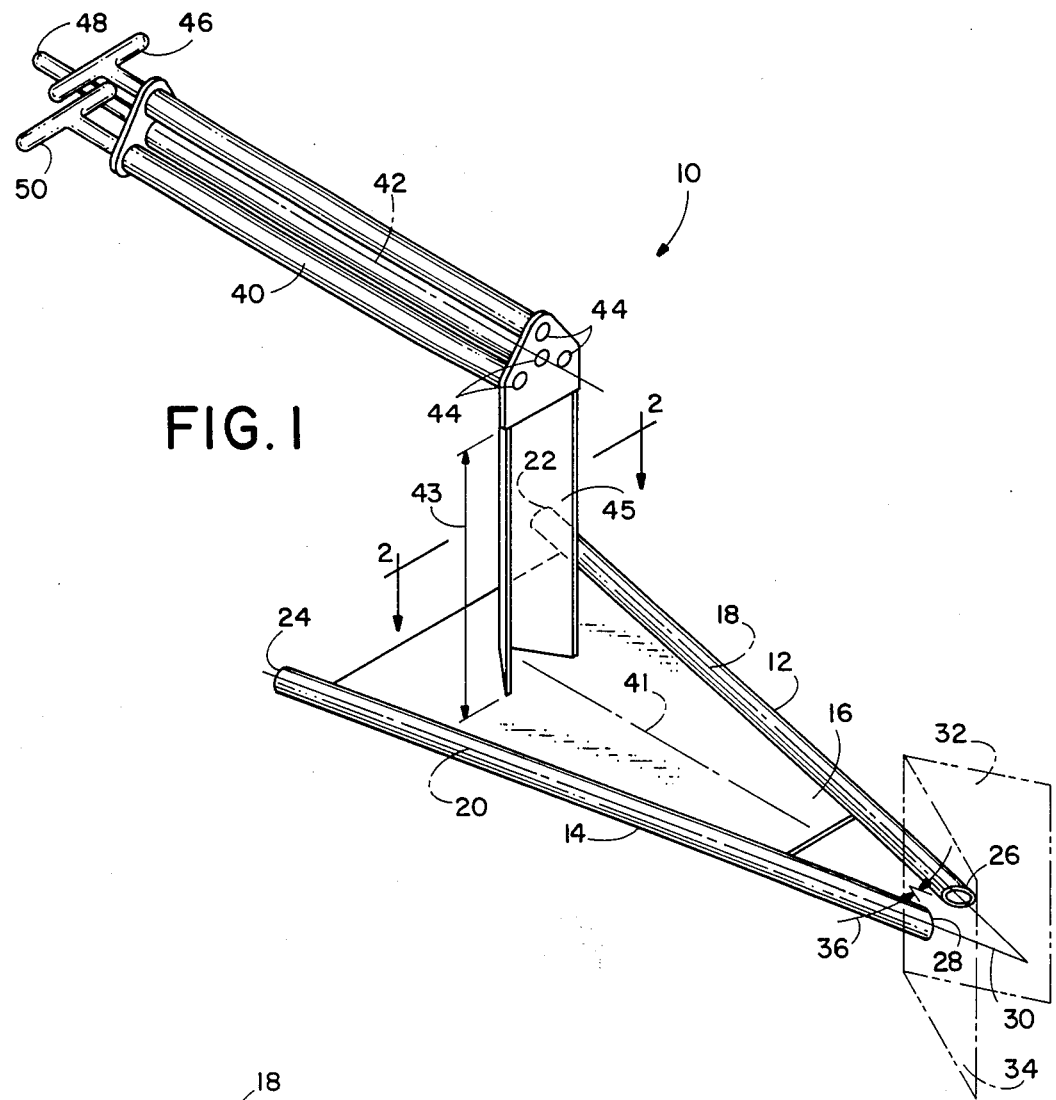
FIG. 1 is a perspective view showing a drilling guide embodying the present invention.

Referring now to the drawings, in FIG. 1, a tool 10 embodying the present invention may be seen to include a pair of convergent tubes 12 and 14 held together by a support plate 16. The tubes 12, 14 have respective tube axes 18, 20, respective rear ends 22, 24 and respective front ends 26, 28. The front ends 26, 28 are separated from one another by a distance of, for example, ⅛ inch, which will be determined to some degree according to the size of the patient's scapula.

The tube axes 18, 20 intersect one another at an imaginary intersection 30 located ahead of the front ends 26, 28 and spaced apart from the closest point of the front ends 26, 28 a predetermined distance 31, preferably between ⅜" and ⅝".

The front ends 26, 28 are preferably terminated at an acute angle to the respective tube axes 18, 20, and the edges of the tubes at the front ends 26, 28 preferably fall in respective imaginary tube front end planes 32, 34 which are perpendicular to the bore plane defined by the tube axes 18, 20. As may be seen in FIG. 2, the tube front end planes 32, 34 define an interior angle 36, while the tube axes 18, 20 intersect to define a bore angle 38. The interior angle may acceptably be within the range of 45°–135° and is preferably about 90°, so that the front ends 26, 28 will rest evenly on the faces of the glenoid rim 72 as shown in FIGS. 6–11. The bore angle 38 should be in the range of 20°–45°, and is preferably about 25°, so as to cause the tube axes 18, 20 to intersect at a desired location within a bone to which it is desired to attach soft tissue according to the invention.

Figure 2:
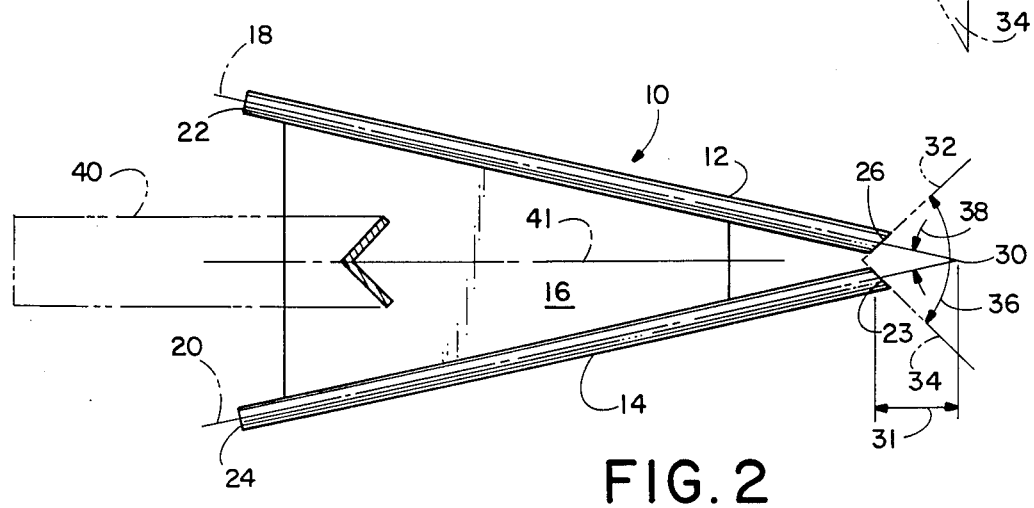
FIG. 2 is a sectional plan view of the convergent tubes of the drill guide portion of the tool shown in FIG. 1, taken along line 2—2.

The tool 10 includes a handle 40, whose longitudinal axis 42 is parallel with an imaginary line 41 lying in the bore plane defined by the tube axes 18 and 20, and substantially bisecting the bore angle 38, as shown in FIGS. 1 and 2. The handle 40 ideally includes three bores 44, each having a diameter substantially equal to the inside diameters of the tubes 12 and 14. The handle 40 may, for example, be made up of four similar tubes all welded together, being spaced apart from the support plate 16 an offset distance 43 of about 2 inches by a handle support leg 45 welded to the support plate 16 and the handle 40.

The bores 44 are useful as storage locations for a locater rod 46, a drill 48, and a suture hook 50. These tools and, if desired, an additional suture hook 50, are conveniently stored in the bores 44 of the handle 40 during sterilization of the tool 10 and to keep the tools together when they are laid out in preparation for use during a Bankart shoulder repair operation.

Figure 3:
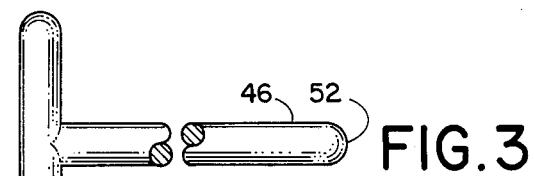
FIG. 3 is a perspective view of the distal end of a locater rod provided for use with the drill guide of the present invention.

As shown in FIG. 3, the locater rod 46 is a straight rod having a length of, for example, six inches, and having a rounded tip 52 and a suitable handle 54 to facilitate manipulation of the locater rod 46, as will be explained in more detail presently.

Figure 4:
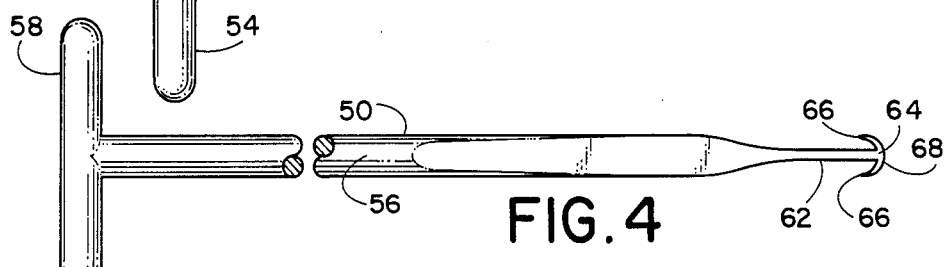
FIG. 4 is a perspective view of the distal end of a suture hook tool used in accordance with the method of the present invention.
Figure 5:
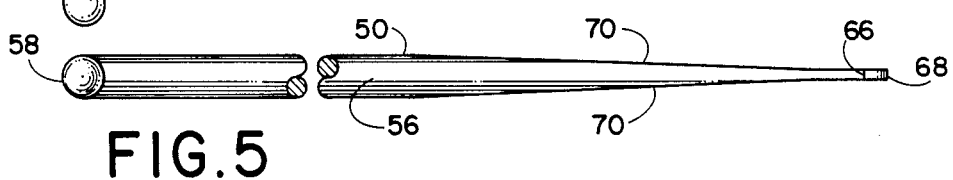
FIG. 5 is another perspective view of the suture hook shown in FIG. 4, showing the hook rotated 90 degrees away from the viewpoint of FIG. 4.

Referring now also to FIGS. 4 and 5, the suture hook 50 is seen to include a shaft portion 56 and a handle 58 similar to those of the locater rod 46. The suture hook 50 is small enough to pass slidingly through either of the tubes 12 or 14. The suture hook 50 has a maximum diameter of, for example, 0.125 inch. A distal portion of the shaft 56 of the suture hook 50 is tapered, as is shown in FIGS. 4 and 5, to a neck 62 of minimum diameter. A hook 64 has a pair of points 66 directed rearwardly toward the handle 58, and an arcuate, transversely oriented front surface 68. A pair of opposite sides 70, located on opposite sides of a plane defined by the points 66 of the hook, are separated from each other by a distance smaller than the diameter of the drill 48, for a distance of approximately 1½ inches from the front surface 68.

Referring now to FIG. 6, the tool 10 is shown being held against the rim 72 of the glenoid cavity 74 in the scapula of a patient who has suffered a shoulder dislocation injury separating a portion of the joint capsule from the glenoid rim 72. After the overlying musculature and tendons have seen retracted to provide access to the shoulder joint, and the joint capsule has been incised in accordance with the Bankart operation procedure, the front ends 26 and 28 of the tubes 12 and 14 are held firmly in contact with the opposite outer and inner faces of the glenoid rim 72 at a location where it is desired to place a suture to reattach a portion of the joint capsule to the glenoid rim 72. It will be appreciated that the imaginary line 41, bisecting the bore angle 38, will be directed toward the glenoid rim 72. The drill 48 fits slidingly within and is guided when drilling by the bore of either of the tubes 12 and 14. A first hole 76 is drilled, for example, into the bone of the scapula guided by the tube 14 as shown in FIG. 6, to a depth great enough to intersect the tube axis 18 of the tube 12. The offset distance 43 separating the handle 40 from the support plate 16 provides clearance for the use of a drill motor. The angular shape of the front ends 26 and 28, forming the interior angle 36 (FIG. 2) facilitates holding the tool 10 securely in the desired position while the first hole 76 is begun.

Once the first hole 76 has been drilled to the desired depth, the drill 48 is withdrawn from the tube 14 and is replaced by the locater rod 46, as shown in FIG. 7. The drill 48 is then inserted through the bore of the tube 12 and is used to bore a second hole 78 into the scapula, entering on the other face of the glenoid rim. During this time, the presence of the locater rod 46, together with continued pressure of the tool 10 against the glenoid rim 72, assures that the second hole 78 will eventually intersect the first hole 76. When the drill 48 has proceeded far enough into the scapula in making the second hole 78, it may contact the locater rod 46, whereupon the locater rod 46 should be withdrawn a short distance, to the position shown in FIG. 8, for example, and the drill 48 may then proceed a short distance farther, so that the second hole 78 intersects the first hole 76. Thereupon, both the drill 48 and the locater rod 46 should be withdrawn from the holes 76 and 78, and may be withdrawn completely from the tool 10. The tool 10 may then be removed from its position against the glenoid rim 72.

Figure 9:
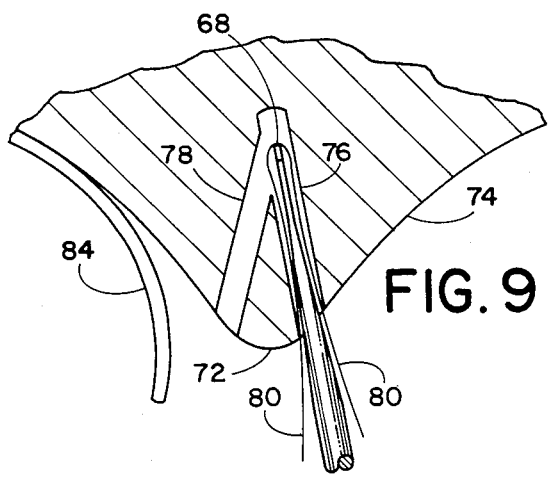
FIG. 9 is a view of the section of a scapula through which a passageway has been prepared in accordance with the method of the invention, showing a suture being inserted through one of the intersecting holes in the scapula.
Figure 10:
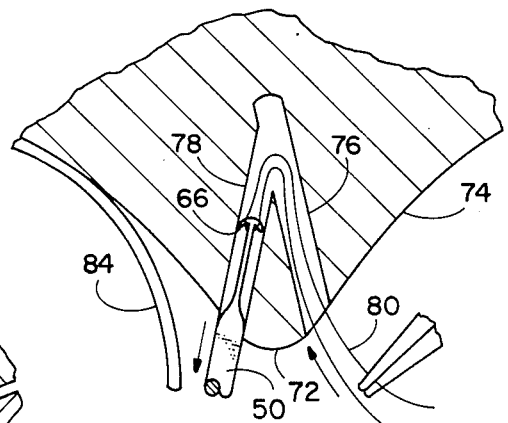
FIG. 10 is a sectional view of the joint shown in FIG. 9, showing the suture hook of the present invention being used to capture a suture which has been inserted into a passageway prepared in the scapula.
Figure 11:
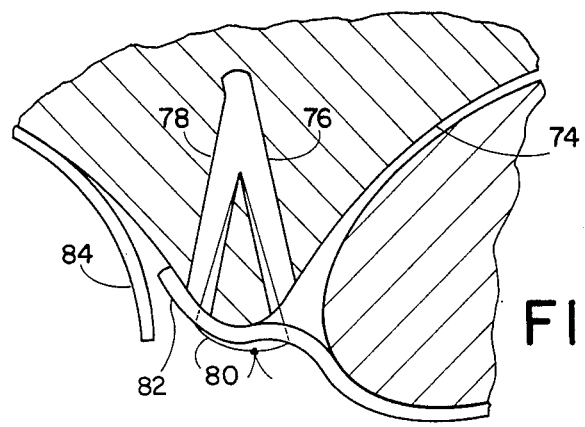
FIG. 11 is a view similar to that of FIGS. 9 and 10, showing a shoulder joint capsule reattached to the scapula according to the present invention.

Preparatory to reattaching the joint capsule to the glenoid rim 72, a suture of suitable strength needs to be inserted through the passageway provided though the glenoid rim 72 in the form of the intersecting first and second holes 76 and 78. This is accomplished by wrapping or folding a medial portion of the suture about the hook 64, extending around the front surface 68, and with a portion of the suture 80 extending along each of the sides 70 of the suture hook 50, as shown in FIG. 9. With the suture 80 so disposed on it, the suture hook 50 is inserted fully into one of the first and second holes 76 and 78. The tapered shape of the suture hook 50 provides clearance for the suture to extend along the sides 70 within the hold. An additional length of the suture 80 is also pushed into the hole hold as far as the intersection with the other hole. The suture hook 50 is then carefully withdrawn, leaving the suture within the hole. Next, the suture hook is inserted into the other one of the holes 76 and 78 and manipulated so that the suture 80 is captured by one of the points 66 of the hook 64. The suture hook 50 is then carefully withdrawn, pulling along with it a portion of the suture 80. One end of the suture 80 is retained to extend from the first hole 76, as shown in FIG. 10. As a result, the suture 80 has its opposite ends extending from the first and second holes 76 and 78, and a strong attachment for the sutures is provided by the bone structure of the glenoid rim 72 included between the first hole 76 and the intersecting second hole 78. As the distance 31 at which the intersection is located ahead of the front ends 26 and 28 of the tubes 12 and 14 is in the range of approximately ⅜ to ⅝ inch, the amount of bone structure retaining the suture 80 is ample to support the load imposed by attachment of the joint capsule to the glenoid rim 72.

The procedure described above for placing the suture 80 in the glenoid rim 72 is repeated at the desired number of locations along the glenoid rim 72, in accordance with the well-known Bankart operational procedure. Thereafter each of the sutures 80 is attached to the lateral margin 82 of the joint capsule and tied to secure the joint capsule to the glenoid rim 72 at each of the several locations, generally in the fashion shown in FIG. 11. Thereafter the medial margin 84 of the joint capsule may be sutured in the usual fashion (not shown) to overlap the lateral margin which has been secured to the glenoid rim 72.

While the tool 10 of the present invention is configured especially for use in connection with the Bankart operation for repair of a shoulder joint, it will be appreciated that the basic features of the present invention may be adapted for use in attaching soft tissue to hard tissue in other locations within the body, particularly as when reattaching ligaments and tendons which have been injured.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of performing the Bankart operation to surgically repair a shoulder joint, comprising:
   (a) providing a drilling guide defining a pair of convergent bores whose axes intersect to define an angle in the range of 20-50 degrees;
   (b) holding said drilling guide so that each of said two convergent bores opens toward a respective face of the anterior rim of the glenoid cavity of the scapula;
   (c) drilling a first hole into the glenoid rim coaxially through a first one of said bores of said drilling guide;
   (d) placing a locating pin through said first bore and into said first hole in the scapula while continuing to hold said drilling guide against the glenoid rim;
   (e) drilling a second hole coaxially through the second one of said pair of bores of the drilling guide and intersecting said first hole within said scapula in the vicinity of said rim;
   (f) pushing a suture into one of said first and second holes in said scapula;
   (g) inserting a hook into the other of said holes and engaging said suture within said scapula with said hook;
   (h) thereafter withdrawing a portion of said suture through said other of said holes; and
   (i) attaching a portion of the capsule of the shoulder joint to said scapula by use of said suture extending through said first and second holes in said scapula.

2. The method of claim 1, including repeating all of the steps of claim 1 a plurality of times.

3. The method of claim 1, including the step of holding a front end of each of said tubes in contact with a respective surface of the glenoid rim of said scapula in order to stabilize said drilling guide while driling said holes.

* * * * *